United States Patent [19]

Schrott et al.

[11] Patent Number: 4,675,423

[45] Date of Patent: Jun. 23, 1987

[54] CAMPHORDITHIOLENE COMPLEXES

[75] Inventors: Wolfgang Schrott, Ludwigshafen; Peter Neumann, Wiesloch; Bernhard Albert, Maxdorf, all of Fed. Rep. of Germany

[73] Assignee: BASF Aktiengesellschaft, Ludwigshafen, Fed. Rep. of Germany

[21] Appl. No.: 826,319

[22] Filed: Feb. 5, 1986

[30] Foreign Application Priority Data

Feb. 20, 1985 [DE] Fed. Rep. of Germany ....... 3505750

[51] Int. Cl.⁴ ................ C07F 15/00; C07F 15/04
[52] U.S. Cl. .................................. 556/136; 556/146; 502/155; 502/522
[58] Field of Search ............................. 556/136, 146

[56] References Cited

U.S. PATENT DOCUMENTS

| | | | |
|---|---|---|---|
| 3,588,216 | 6/1971 | Bloom | 556/136 X |
| 3,928,477 | 12/1975 | Field et al. | 556/146 X |
| 4,508,655 | 4/1985 | Sasagawa et al. | 556/136 |
| 4,593,113 | 6/1986 | Kauffman | 556/136 |

*Primary Examiner*—Helen M. S. Sneed

*Attorney, Agent, or Firm*—Oblon, Fisher, Spivak, McClelland & Maier

[57] ABSTRACT

Dithiolene complexes of the formula

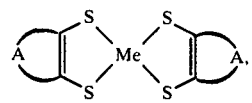

where Me is nickel, palladium or platinum, and <A is

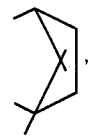

are readily soluble in organic solvents and have a high absorption in the range from 750 to 850 nm and are therefore very useful for optical recording media.

The complexes may furthermore be used as antioxidants, stabilizers, corrosion inhibitors or catalysts, or as protective layers for colored photographic layers.

4 Claims, No Drawings

CAMPHORDITHIOLENE COMPLEXES

The literature discloses a large number of binary dithiolene complexes of the general formula

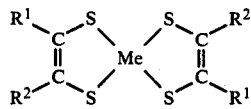

where $R^1$ and $R^2$ and the central metal Me vary over a wide range. $R^1$ and $R^2$ can each be hydrogen or alkyl, unsubstituted or substituted aryl, CN, $CF_3$, SR or other radicals. In addition to the binary complexes, ternary dithiolene complexes of the formula

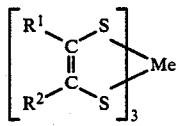

are also known. A summary is given by J. A. McCleverty in Progr. Inorg. Chem. 10 (1968), 49–221, and G. N. Schrauzer in Acc. Chem. Res. 2 (1969), 72–80.

In particular, the planar binary metal complexes (I) in which Me is nickel, palladium or platinum and which have an intense absorption between about 750 and 950 nm have been thoroughly investigated and used as IR dyes for optical recording media or laser components and IR absorbers for lenses for spectacles, filters and other optical applications.

Dithiolene complexes (I) in which $R^1$ and $R^2$ are each an aromatic radical have a large, planar chromophore and, depending on the central metal atom (Me), therefore exhibit either a strong intermolecular interaction between the metal atoms and the sulfur atoms, which leads to band structures, or a pronounced tendency to crystallization, the complexes melting with decomposition at fairly high temperatures. For many applications, adequate solubility in organic solvents and/or binders is required. In many cases, this can only be achieved by substitution of the dithiolene chromophore with long-chain alkyl, phenylalkyl, alkoxy or alkylamino radicals by an expensive procedure.

It is an object of the present invention to provide dithiolene complexes which are easily obtainable and readily soluble in the plastics conventionally used for the production of recording media.

We have found that this object is achieved and that dithiolene complexes of the formula

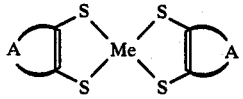

where Me is nickel, palladium or platinum and <A is

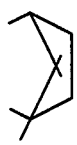

meet the requirements set.

The novel dithiolene complexes occur in the form of the cis- and trans-isomers

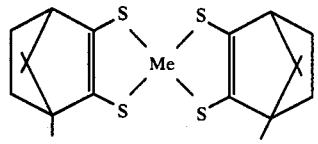

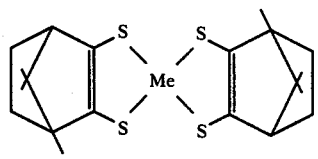

or in the form of mixtures of these isomers.

The dithiolene complexes (III) are readily or very readily soluble in organic solvents and in plastics. The novel complexes can also be readily sublimed under greatly reduced pressure.

Because of these properties, (III) has a wide range of possible uses. (III) can be applied in the form of thin layers either by vapor deposition under reduced pressure or by a wet procedure by knife coating or whirler coating from solutions in the presence or absence of a binder.

Depending on the central metal atom (Me) selected for III, these novel dithiolene complexes can be used, for example, as stabilizers for protecting polymers and organic materials from oxidative damage (cf. DE-A-1 941 203), as antioxidants and corrosion inhibitors (cf. U.S. Pat. No. 4,427,560) or as protective layers for colored photographic layers or dyeings on textiles (DE-A-2 456 075). It appears that they may also be used as catalysts, for example for the decomposition of peroxides (GB-A-1 263 910), for the preparation of phenols and ketones, and for the catalyzed photochemical production of hydrogen by the process described in U.S. Pat. No. 4,325,793.

The novel IR dyes (III) are preferably used for the preparation of optical recording media.

The complexes (III) are obtainable in good yields according to the following equation:

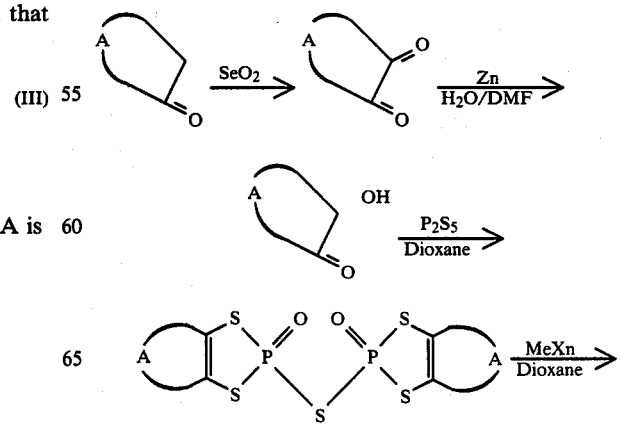

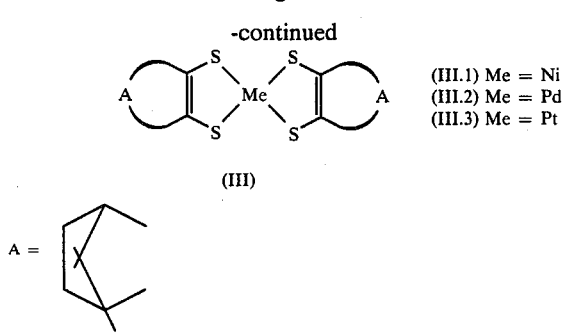

(III.1) Me = Ni
(III.2) Me = Pd
(III.3) Me = Pt

When optically active or racemic camphor is used as a starting material and the procedure described by H. Rupe and A. T. di Vignano, Helv. Chim. Acta 20 (1937), 1078, is employed, camphorquinone is obtained in 90% yield. This is reduced to α-hydroxycamphor [W. Kreiser, Liebigs Ann. Chem. 745 (1971), 164]. In a modified method due to G. N. Schrauzer, J. Amer. Chem. Soc. 87 (1965), 1483–1489, the α-hydroxyketone is converted with phosphorus pentasulfide to an organophosphorus intermediate which, without being isolated but after the inorganic components have been filtered off, is reacted with the corresponding metal salt to give the particular dithiolene complex (III).

The physical and spectroscopic data for the novel compounds (III) are summarized in the experimental section.

Owing to the advantages of solid injection lasers, optical recording systems of great interest are those which can be written on and read by means of these lasers, i.e. the optical recording media must have a high absorption in the region of these lasers (between about 700 and 900 nm).

Known dyes for such optical recording media are, in particular, substituted phthalocyanines containing various central metal atoms, azo-metal complex dyes containing chromium or cobalt as the central atom, and dithiolene complexes containing nickel, palladium or platinum.

The dyes were applied onto the base by vapor deposition or by coating. In this context, reference may be made to the following prior art: U.S. Pat. Nos. 4,458,004 and 4,241,355, Nos. EP-A-13 453, 83 991 and 84 729, and Nos. JP-A-67 093/1984, 82 095/1982 and 82 096/1982. The structure and preparation of the optical recording media are known (U.S. Pat. No. 4,320,489 and Nos. DE-A-2 951 341, 3 319 738 and 3 032 135).

The novel dithiolene complexes (III) can be processed to optical recording media by a known method, either alone or as a mixture with other dyes.

The layer containing the complexes (III) is preferably applied by knife coating, immersion or, in particular, whirler coating using dissolved or dispersed (III). Metallic reflective layers are preferably applied by vapor deposition. It is also possible to apply suitable metal foils.

To apply the absorption layers from solution, a solution or, if appropriate, a dispersion of the dye or dye mixture and of the polymer in a suitable solvent, such as methylene chloride, chloroform, carbon tetrachloride, acetone, methyl ethyl ketone, cyclohexanone, toluene, acetonitrile, ethyl acetate or methanol, or a mixture of these, is prepared, and, if required, a binder is added.

Suitable binders are either radiation-curable or heat-curable resins, eg. photopolymers, silicone resins or epoxy resins, or thermoplastics.

Thermoplastics exhibiting very little, if any, crystallinity and having a glass transition temperature of >35° C., in particular >75° C., are preferred. Moreover, the plastics must be very compatible with the novel thiolene compounds. Examples of suitable binders are water-insoluble binders having a high dissolving power for the thiolene compound, eg. (meth)acrylate polymers and copolymers, polystyrene homopolymers and copolymers, polyvinyl carbazole, polyvinyl ester copolymers, polyvinyl chloride and cellulose esters. The heat evolved when the laser light is absorbed causes radial flow of the thermoplastic in an outward direction and hence the formation of sharp-edged holes, coupled with excellent signal/noise characteristics for the information.

This dye formulation is then applied onto a substrate (subbing layer) which has been cleaned or pretreated beforehand, by knife coating, immersion or, preferably, whirler coating, and the layer is dried or cured in the air. The film can also be dried or cured under reduced pressure at elevated temperatures, or, if required, using radiation.

Depending on the structure of the system, the dye-in-polymer layer is first applied, followed by the reflector, or vice versa. If appropriate, the application of intermediate and protective layers or of a reflecting layer can be dispensed with.

The Examples which follow illustrate the invention. Percentages are by weight.

EXAMPLE 1

Biscamphenyldithio-nickel (III.1)

10.1 g (60 millimoles) of optically active α-hydroxycamphor, 7.9 g (60 millimoles) of ammonium sulfate and 44.4 g (0.2 mole) of phosphorus pentasulfide are suspended in 100 ml of dioxane, and the suspension is refluxed for 2 hours. It is cooled to room temperature and then filtered, and the residue is washed with about 20 ml of dioxane. A solution of 7.2 g (30 millimoles) of nickel(II) chloride hexahydrate in 30 ml of water is added to the filtrate, and the mixture is refluxed for 2 hours. The reaction solution is slowly cooled, a dark green precipitate separating out. The precipitate is filtered off under suction, washed with a little cold dioxane, then with water and finally with a little ethanol, and dried under reduced pressure to give 10.5 g (77% of theory) of crude product, which gives only a small starting spot when subjected to thin layer chromatography (silica gel/toluene: $R_f$=0.63). Filtration over a short silica gel column gives analytically pure (III.1).

Mp.: 280°–285° C.

$C_{20}H_{28}NiS_4$ (455): calculated: C 52.8; H 6.2; S 28.1; Ni 13.0%; found: C 52.7; H 5.9; S 27.9; Ni 13.0%;

UV $\lambda_{max}$=786 nm, $\epsilon$=23,530 (methylene chloride); $\lambda_{max}$=794 nm, $\epsilon$=23,580 (toluene).

IR (KBr): $\gamma$=2958, 1342, 1282, 1247, 1204, 1182, 1160, 1107, 1071, 684 cm$^{-1}$.

$^1$H-NMR (CDCl$_3$): $\delta$=0.65 S [6H], 0.95 S [6H], 1.25 d [4H], 1.40 s [6H], 1.82 t [2H], 2.08 d(t) [2H], 3.12 d [2H].

$^{13}$C-NMR (CDCl$_3$): $\delta$=11.5, 20.3 (2C), 26.0, 33.0, 59.9, 61.4, 62.0, 193.7, 198.5.

MS (70 eV): m/e=454 (100%) M⊕ [Ni⁵⁸]+Ni isotope pattern; 411 (60%) M⊕ [Ni⁵⁸]-C₃H₇+Ni isotope pattern.

EXAMPLE 2

Bis-camphenyldithio-palladium (III.2)

5.05 g (30 millimoles) of optically active α-hydroxycamphor, 4.0 g (30 millimoles) of ammonium sulfate and 9.8 g (44 millimoles) of phosphorus pentasulfide are suspended in 80 ml of dioxane, and the suspension is refluxed for 2 hours. It is cooled to room temperature and then filtered, and the residue is washed with 20 ml of dioxane. A solution of 1.63 g (5 millimoles) of potassium tetrachloropalladate(II) in 32.5 ml of water is added to the filtrate, and the mixture is again refluxed for 2 hours. The reaction mixture is cooled, washed with 10 ml of cold dioxane and taken up in a very small amount of methylene chloride, and the solution is filtered over a 10 cm long column (silica gel 60). The violet fraction gives 2.2 g (88% of theory) of analytically pure palladium complex (III.2).

Mp.: 278°–281° C.

$C_{20}H_{28}PdS_4$ (502): calculated: Pd 21.1%; found: 19.8%

UV: $\lambda_{max}$=830 nm, $\epsilon$=28,322 (methylene chloride); 833 nm, $\epsilon$=27,663 (toluene); 834 nm, $\epsilon$=19,559 (dimethylformamide).

IR (KBr): $\gamma$=2956, 1339, 1292, 1285, 1247, 1207, 1182, 1160, 1107, 1073, 687, 564, 433 cm⁻¹.

¹H-NMR (CDCl₃): δ=0.78 s [3H], 0.82 S [3H], 0.97 S [6H], 1.34 s [6H], 1.34–1.45 m [4H], 1.87 t [1H], 1.88 t [1H], 2.15 m [2H], 2.98 S [1H], 3.01 s [1H].

¹³C-NMR (CDCl₃): δ=11.15, 20.35, 20.44, 26.73, 33.78, 60.80, 61.20, 61.36, 62.66, 195.72, 195.98, 200.36, 200.48.

MS (70 eV): m/e=502 (100%) M⊕[Pd¹⁰⁶]+isotope pattern; 459 M⊕[Pd¹⁰⁶]-C₃H₇+isotope pattern.

EXAMPLE 3

Biscamphenyldithio-platinum (III.3)

4.8 g (28.8 millimoles) of optically active α-hydroxycamphor, 3.8 g (28.8 millimoles) of ammonium sulfate and 9.8 g (44 millimoles) of phosphorus pentasulfide are suspended in 100 ml of dioxane, and the suspension is refluxed for 2 hours. It is cooled to room temperature and then filtered, and the residue is washed with about 20 ml of dioxane. A solution of 2.0 g (4.8 millimoles) of potassium tetrachloroplatinate(II) in 33 ml of water is added to the filtrate, and the mixture is again refluxed for 2 hours. The reaction mixture is slowly cooled, a finely crystalline violet precipitate separating out. The isolated precipitate is washed with a little cold dioxane, then with water and finally with ethanol, after which it is dried under reduced pressure. The crude product (2.5 g, 88% of theory) has a small starting spot when subjected to thin layer chromatography (silica gel/toluene: R$_f$=0.63; methylene chloride: R$_f$=0.92). When the solution in methylene chloride is filtered over a short column containing silica gel, (III.3) is obtained in pure form. Yield: 2.3 g (81% of theory).

Mp. 301°–302° C.

$C_8H_{28}PtS_4$ (591): calculated: C 40.6; H 4.7; S 21.7; Pt 33.0%; found: C 40.8; H 4.9; S 21.6; Pt 34.3%;

UV: $\lambda_{max}$=776 nm (methylene chloride); 768 nm, $\epsilon$=45,030 (toluene).

IR (KBr). $\gamma$=2957, 1344, 1293, 1285, 1248, 1207, 1182, 1161, 1109, 1071, 689 cm⁻¹.

¹³C-NMR (CDCl₃): δ=11.55, 20.08, 21.01, 26.33, 26.40, 33.31, 33.36, 59.10, 59.46, 59.81, 61.11, 61.43, 61.60, 61.67, 191.13, 191.39, 195.98, 196.07.

MS (70 eV): m/e=590, 591 (100%), 592, 593, 595 M⊕ (isotope peaks), 547, 548, 549, 550 M⊕ (isotope peaks)-C₃H₇.

EXAMPLE 4

Biscamphenyldithio-nickel (III.1)

When 10.1 g (60 millimoles) of racemic α-hydroxycamphor, 7.9 g (60 millimoles) of ammonium sulfate, 44.4 g (0.2 mole) of phosphorus pentasulfide and 7.2 g (30 millimoles) of nickel(II) chloride hexahydrate are used as starting materials and the same reaction conditions and working up conditions as in Example 1 are employed, 4.3 g (31% of theory) of nickel complex (III.1) are obtained. This product is characterized as follows:

Thin layer chromatography (silica gel/toluene): R$_f$=0.62.

Mp.: 270°–276° C.

UV: $\lambda_{max}$=786 nm, $\epsilon$=23,010 (methylene chloride).

IR (KBr): $\gamma$=2958, 1343, 1292, 1285, 1249, 1257, 1181, 1161, 1108, 1070, 730, 562, 440 cm⁻¹.

¹H-NMR (CDCl₃): δ=0.65 s [6H], 0.96 s [6H], 1.24 S [2H], 1.28 s [2H], 1.42 S [6H], 1.83 t [2H], 2.09 d (t) [2H], 3.09 d [2H].

¹³C-NMR (CDCl₃): δ=11.47, 20.25 (2C), 25.97, 33.01, 59.85, 61.35, 62.00, 193.65, 198.41.

MS (70 eV): m/e=454 (100%) M⊕ [Ni⁵⁸]-H+isotope pattern; 411 (55%) M⊕ [Ni⁵⁸]-C₃H₇+isotope pattern.

EXAMPLE 5

Biscamphenyldithio-palladium (III.2)

8.4 g (50 millimoles) of racemic α-hydroxycamphor, 6.6 g (50 millimoles) of ammonium sulfate and 17 g (75 millimoles) of phosphorus pentasulfide are suspended in 75 ml of dioxane, and the suspension is refluxed for 2 hours. It is cooled to room temperature and then filtered, and the residue is washed with 20 ml of dioxane. A solution of 33 g (10 millimoles) of potassium tetrachloropalladate(II) in 50 ml of water is added to the filtrate, and the mixture is again refluxed for 2 hours. The reaction mixture is cooled, the oily, partially crystalline product is filtered off and taken up in methylene chloride, and the solution is washed with water and dried. The crude product is dissolved in 25 ml of toluene, and the solution is chromatographed over a 50 cm column containing alumina. The violet fraction gives 3.6 g (72% of theory) of (III.2).

Mp.: 275°–277° C. (after sublimation)

$C_{20}H_{28}PdS_4$ (502): calculated: Pd 21.2%; found: Pd 19.9%

UV: $\lambda_{max}$=836 nm (methylene chloride); 823.5 (methanol); 837 nm, $\epsilon$=20,860 (toluene).

EXAMPLE 6

Biscamphenyldithio-platinum (III.3)

4.8 g (29 millimoles) of racemic α-hydroxycamphor, 3.8 g (29 millimoles) of ammonium sulfate, 9.8 g (44 millimoles) of phosphorus pentasulfide and 2.0 g (4.8 millimoles) of potassium tetrachloroplatinate(II) are used as starting materials, and the procedure described in Example 3 is followed. 1.9 g (67% of theory) of platinum complex (III.3) are obtained, this product being characterized as follows:

Thin layer chromatography (silica gel/methylene chloride): $R_f = 0.92$.

Mp.: 265°–275° C.

UV: $\lambda_{max} = 769$ nm, $\epsilon = 39{,}810$ (toluene).

IR (KBr): $\gamma = 2957, 1344, 1293, 1285, 1249, 1207, 1182, 1161, 1109, 1070, 681, 560, 430$ cm$^{-1}$.

$^1$H-NMR (CDCl$_3$): $\delta = 0.71$ S [3H], 0.73 s [3H], 0.96 S [6H], 1.25–1.40 m [4H], 1.40 s [6H], 1.80 t [2H], 1.98–2.12 m [2H], 3.06 d [2H].

MS (70 eV): m/e = 590, 591 (100%), 592, 593, 594 M⊕ (isotope pattern), 547 (60%) + isotope pattern.

EXAMPLE 1 OF USE

A 1.2 mm thick polymethyl methacrylate disk which has a diameter of 120 mm and whose inner hole has a diameter of 15 mm is cleaned beforehand (removal of dust particles) and provided with a subbing layer about 0.3 μm thick and consisting of high molecular weight polymethyl methacrylate, this being done under cleanroom conditions. A solution of 1 g of the dye (III.3) and 1 g of a 70:30 methacrylate/methacrylic acid copolymer in chloroform is applied onto the subbing layer by whirler coating at 4800 rpm, the solvent evaporating off and a stable dye-containing polymer layer about 0.3 μm thick being formed. A 0.03 μm thick aluminum reflector is applied onto the dye layer in a reduced-pressure vapor deposition apparatus, and a 1.2 μm thick protective layer of polystyrene in xylene is applied onto this by whirler coating.

Two such disks are bonded with one another via suitable spacer rings, the coated sides facing inward, to form a sandwich, so that an air gap of about 0.4 mm remains between the disks. A tuned AlGaAs laser is used to inscribe individual holes of about 1 μm in the sensitive layer, this being done both in the individual disks and in the sandwich recording medium. This information in the form of holes can be read by means of semiconductor laser light. The best sensitivity and a very good signal-to-noise ratio is obtained using laser light of wavelength $\lambda = 780$ nm.

EXAMPLE 2 OF USE

The procedure described in Example 1 of use is followed, except that a solution of 0.045 g of the dye (III.1), 0.05 g of the dye (III.2), 0.06 g of the dye (III.3) and 0.2 g of polymethyl methacrylate in 6 ml of methylene chloride is used in order to apply the dye-in-polymer layer.

EXAMPLE 3 OF USE

The procedure described in Example 1 of use is followed, except that the layer which is sensitive to laser light is produced by vaporizing III.3 under reduced pressure from a tantalum boat (T = 200° C., p ≤ 10$^4$ mm Hg). The layer is about 300 Å thick.

We claim:

1. A dithiolene complex of the formula

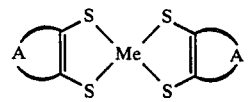

where Me is nickel, palladium or platinum, and <A is

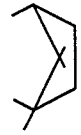

2. A dithiolene complex as claimed in claim 1, wherein Me is nickel.

3. A dithiolene complex as claimed in claim 1, wherein Me is palladium.

4. A dithiolene complex as claimed in claim 1, wherein Me is platinum.

* * * * *